United States Patent [19]

Moriya

[11] 4,179,931
[45] Dec. 25, 1979

[54] PNEUMATIC METAL SAMPLER

[75] Inventor: Kazuo Moriya, Tokyo, Japan

[73] Assignee: Richard A. Falk, Hartland, Wis.

[21] Appl. No.: 942,511

[22] Filed: Sep. 15, 1978

[51] Int. Cl.² .............................................. G01N 1/12
[52] U.S. Cl. ............................ 73/425.6; 73/DIG. 9
[58] Field of Search ......... 73/425.4 R, 425.6, DIG. 9; 164/4

[56] References Cited

U.S. PATENT DOCUMENTS

| | | | |
|---|---|---|---|
| 3,589,199 | 6/1971 | Levin | 73/425.6 |
| 3,915,002 | 10/1975 | Hance | 73/DIG. 9 |
| 4,140,019 | 2/1979 | Falk | 73/DIG. 9 |

Primary Examiner—S. Clement Swisher
Attorney, Agent, or Firm—Henry C. Fuller

[57] ABSTRACT

Disclosed herein is a pneumatic molten metal sampler for pneumatically obtaining a sample of metal which includes an elongated fill tube which is secured to the side of a paperboard sleeve by refractory cement and projects beyond the end of the paperboard sleeve for immersion in a molten melt. A bend on the fill tube discharges into the sample cavity intermediate the ends of the cavity. A vent construction at the end of the cartridge affords communication with a vacuum pump but prevents loss of metal from the sample cavity.

5 Claims, 4 Drawing Figures

U.S. Patent     Dec. 25, 1979     4,179,931
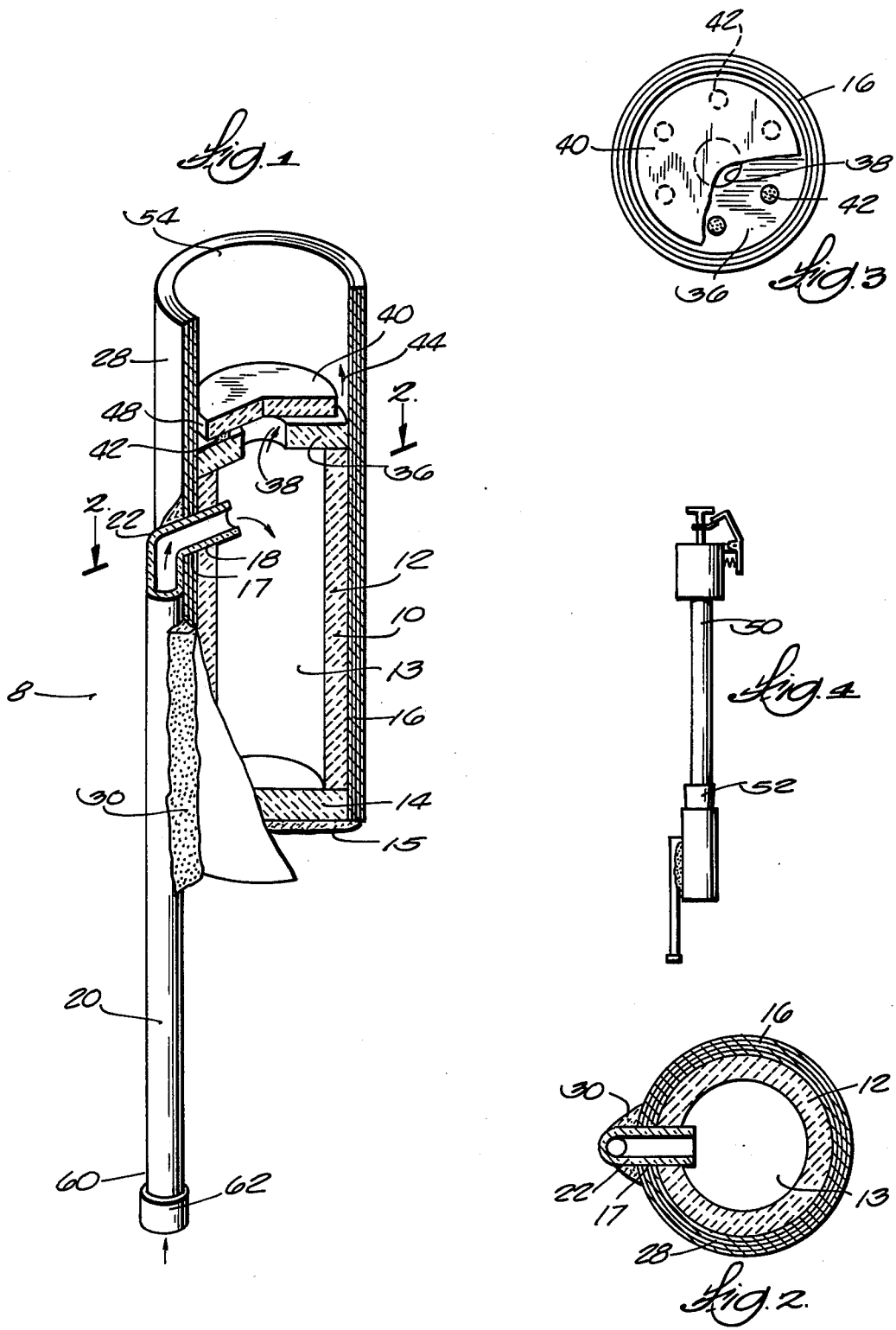

PNEUMATIC METAL SAMPLER

BACKGROUND OF THE INVENTION

In the sampling of molten metal, pneumatic samplers have been developed to withdraw molten metal into a sample cavity without complete immersion of the cartridge. Pat. Nos. 3,791,220; 3,905,238; and 3,996,803 disclose pneumatic samplers in which the pressure is reduced in the mold cavity to effect evacuation of the molten metal into the mold cavity. Although pneumatic samplers of the types illustrated in the foregoing patents have particular advantages in certain applications and for certain categories of metal melts, there are some disadvantages. Molten metal can run out the fill tube during and after withdrawal from the bath and shrinkage cavities can occur. Furthermore, voids can occur in the sample.

Side entry port sampling cartridges such as that shown in U.S. Pat. No. 3,481,201, and particularly that illustrated in FIG. 5 of that patent, provide good samples and there is no loss of molten metal as the sample cartridge is withdrawn from the melt. The top filling of the sample eliminates voids in the sample. In addition, side fill cartridges tend to minimize the shrinkage cavity.

SUMMARY OF THE INVENTION

The invention provides a pneumatic sampler which has the advantages of a side entry fill port and a pneumatic sampler. The sampler includes a refractory sample cartridge positioned in a paperboard sleeve. A pump such as that illustrated in U.S. Pat. No. 3,791,220 can be employed to evacuate the same cavity in the refractory cartridge. An elongated fill tube is provided in which the elongated tube discharges into a side entry port intermediate the upper end of a generally vertically disposed sample cavity. To minimize or eliminate metal flow into the pump or pump pipe, an end wall assembly for the cartridge affords communication of the pump with the sample cavity to evacuate the cavity but has a deflector disc to prevent entry of metal into the pump. The elongated fill tube enables use of the sampler where complete immersion of the sampler is not desired and the side entry fill arrangement minimizes voids and shrinkage.

The sampler of the invention provides vacuum induced flow through the fill tube with gravity flow from the fill tube into the sampler.

Further objects, advantages and features of the invention will become apparent from the following disclosure.

DESCRIPTION OF THE DRAWINGS

FIG. 1 is an elevational view in fragmentary section showing the sampler of the invention.

FIG. 2 is a sectional view along line 2—2 of FIG. 1.

FIG. 3 is an end view of the upper end of the cartridge partially broken away.

FIG. 4 is a view in reduced scale of a pneumatic pump and the sampler shown in FIG. 1.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIG. 1 illustrates a sampler 8 in accordance with the invention which includes a refractory sample carriage 10 which has a cylindrical refractory wall 12 which surrounds a sample cavity 13 which is closed at the bottom by a refractory disc 14 secured in place by refractory cement 15. The refractory cartridge 10 is located in an insulating sleeve 16 preferably of paperboard. The refractory wall 12 is provided with a side entry molten metal fill port 18.

In accordance with the invention, a fill tube 20 is provided which can be fused quartz and which can be of various lengths but is preferably longer than the cartridge and projects a distance from the end of the cartridge so that the cartridge does not have to be immersed in the metal. The fill tube 20 is provided with a fill tube portion 22 at right angles with the tube 20. The portion 22 extends through an aperture 17 in sleeve 16 and the side entry port 18 for discharge into the cavity 13. The portion 22 can either be integrally formed with the fused quartz tube 20 by a bend or can be a separate piece connected along a 45° mitered edge to tube portion 20. The tube 20 is secured to the outer surface 28 of the paperboard sleeve by a bead of refractory cement 30, which also can provide an air seal for portion 22 with respect to aperture 17 in sleeve 16.

The upper end of the cartridge is provided with means to afford evacuation of the sample cartridge cavity 13 to withdraw metal through the fill tube 20 but prevent metal flow into the pump. In the disclosed construction the means includes an end wall 36 provided with an aperture 38. The end wall 36 can be secured to or within the wall 12 by refractory cement. Above the aperture 38 in spaced relation is a deflector disc 40 which is secured to the end wall 36 and spaced therefrom by a series of circumferentially spaced beads 42 of refractory cement. This provides an air flow or pressure communication path as indicated by arrows 44. The disc 40 has a diameter less than the diameter of the end wall 36 to provide clearance at 48 with the sleeve 16. FIG. 4 illustrates a pneumatic pump or evacuating device similar to that disclosed in U.S. Pat. No. 3,996,803, with a pipe 50 which has a tapered plug 52 which interfits in the open end 54 of the sleeve 16 to provide a pressure seal.

In use, the sampler of the invention is generally vertically disposed and the end 60 of tube 20 is immersed in the melt. The end 60 can be provided with a fusible cap 62 for penetration of slag. When the end 60 is positioned at the desired level in the melt, the release on the pump is actuated to cause withdrawal of the piston and evacuation or pressure reduction in the sample cavity to cause metal flow into the fill tube and gravity filling of cavity 13.

The disclosed sampler is particularly useful for making elongated samples of six inches or more for Jominey tests.

What is claimed is:

1. A molten metal sampler having cartridge wall means including a side wall and end walls defining a sample cavity for forming a sample for analysis, said side wall means having an aperture defining a side entry fill port for filling said cavity, said aperture being located intermediate the end walls, a fill tube having one end communicating with said fill port in said sampler and the other end remote from said fill port for immersion in a molten metal melt, vent means for said cavity, and pressure reducing apparatus in communication with said cavity through said vent means for reducing the pressure in said cavity and said fill tube to withdraw molten metal into said fill tube where it flows by gravity to fill the sample cavity and wherein said fill tube is secured to said housing by refractory cement.

2. A molten metal sampler having cartridge wall means including a side wall and end walls defining a sample cavity for forming a sample for analysis, said side wall means having an aperture defining a side entry fill port for filling said cavity, said aperture being located intermediate the end walls, a fill tube having one end communicating with said fill port in said sampler and the other end remote from said fill port for immersion in a molten metal melt, vent means for said cavity, and pressure reducing apparatus in communication with said cavity through said vent means for reducing the pressure in said cavity and said fill tube to withdraw molten metal into said fill tube where it flows by gravity to fill the sample cavity and in which said fill tube has a transverse portion extending into said side entry port and a second portion extending beyond an end wall and generally parallel to but offset from the longitudinal axis of said cavity.

3. A molten metal sampler having cartridge wall means including a side wall and end walls defining a sample cavity for forming a sample for analysis, said side wall means having an aperture defining a side entry fill port for filling said cavity, said aperture being located intermediate the end walls, a fill tube having one end communicating with said fill port in said sampler and the other end remote from said fill port for immersion in a molten metal melt, vent means for said cavity, and pressure reducing apparatus in communication with said cavity through said vent means for reducing the pressure in said cavity and said fill tube to withdraw molten metal into said fill tube where it flows by gravity to fill the sample cavity and including a protective sleeve enclosing said cartridge and said vent means comprising an aperture in said cartridge end wall, a deflector disc connected to and spaced from said end wall in opposed relationship and sized to provide an annular vent space between said disc and said sleeve to afford communication of said sample cavity with a pump through said vent space.

4. A molten metal sampler having cartridge wall means including a side wall and a top wall and a bottom wall defining a sample cavity for forming a sample for analysis, said side wall means having an aperture defining a side entry fill port for filling said cavity, said side entry port being intermediate said top and bottom walls, a fill tube having a transverse portion extending through said fill port into said sample cavity and another fill tube portion extending along said cartridge side wall and past said bottom wall for immersion in molten metal, vent means for said cavity, and wall means on said sampler for connection to pressure reducing apparatus for reducing the pressure in said cavity and said fill tube to withdraw molten metal into said fill tube where it flows by gravity to fill the sample cavity.

5. A sampler in accordance with claim 4 wherein said wall means defining a sample cavity is located in a protective housing and said fill tube extends along said housing in abutting contact therewith and is secured thereto.

* * * * *